United States Patent [19]
Barth et al.

[11] 4,115,195
[45] Sep. 19, 1978

[54] RABIES VACCINE PREPARATION

[75] Inventors: Rudolph Barth, Marburg, Lahn; Oskar Jaeger, Niederwetter, both of Fed. Rep. of Germany

[73] Assignee: Behringwerke Aktiengesellschaft, Marburg, Lahn, Fed. Rep. of Germany

[21] Appl. No.: 786,766

[22] Filed: Apr. 12, 1977

[30] Foreign Application Priority Data

Apr. 14, 1976 [DE] Fed. Rep. of Germany ....... 2616407

[51] Int. Cl.² ...................... C12K 7/00; A61K 39/28; C12K 5/00
[52] U.S. Cl. ........................................ 195/1.3; 424/89
[58] Field of Search ............................ 195/1.3; 424/89

[56] References Cited

U.S. PATENT DOCUMENTS

2,768,114  10/1956  Koprowski ........................ 195/1.3

*Primary Examiner*—Sam Rosen
*Attorney, Agent, or Firm*—Curtis, Morris & Safford; Biebel, French & Nauman

[57] ABSTRACT

A rabies vaccine is prepared by adaptation of the rabies virus to chick-embryo fibroplast cell cultures in progressing dilutions of from $10^{-1}$ to $10^{-5}$ for the inoculation of the cell culture passages and for multiplication in dilutions of from $10^{-2}$ to $10^{-5}$ for inoculation of the growth cultures.

4 Claims, No Drawings

RABIES VACCINE PREPARATION

This invention relates to a rabies vaccine and to a process for its preparation.

Inactivated vaccines and virus vaccines for the immunization against rabies are known. The inactivated rabies vaccines consist of suspensions of virus-containing central nervous tissue of infected animals, such as rabbits or sheep, or of suspensions of infected duck fetuses. Vaccines of this type have the draw-back that, due to the high content of foreign proteins, they may cause undesired side effects at the point of injection as well as of general nature. When rabies vaccines from the central nervous tissue are used, the patient may even suffer from neurocomplications with permanent damage, all the more since a series of injections is required for a sufficient protection against rabies. It has been ascertained that similar side effects also occur with animals.

Attempts have been made to propagate the rabies virus in tissue cultures of cell strains of baby hamster kidneys, for example BHK 21-cells, in NIL cells, in primary cells of hamster kidneys, or in chick-embryo fibroblast cells, and to prepare therefrom inactivated vaccines for animals. To obtain rabies virus vaccines for animals, primary cells of kidneys of pigs or hamsters or cell strains of kidney cells of dogs or bovine are being used. In these cases, the virus concentrations as obtained with central nervous system material cannot be reached. A sufficiently high virus titer is, however, the prerequisite to an effective rabies vaccine, especially to an inactivated vaccine. Some of the cells used have the further drawback that they may cause malignant tumors.

It is not possible to use a serum yielding higher concentrations of virus during the growth of the virus in the cell culture, as the foreign serum would lead to the formation of undesired antibodies. To overcome this difficulty, an additional procedure of concentrating the virus-containing solution, for example a precipitation, centrifugation or ultra-filtration, has been inserted into the production line, i.e. measures by which the process of preparation becomes more difficult and more expensive.

In the case of test vaccines for use in animals, maximum titers of $10^{5.0}$ to $^{6.0}$ PFU/ml (plaque forming units/ml) or of $6.1 \times 10^6$ baby mouse LD$_{50}$/ml (LD = lethal dose) have been described with chick-embryo fibroblast cells, i.e. titers which do not ensure a good immunization.

It is an object of the present invention to provide a process for the preparation of a rabies vaccine by adapting the rabies virus to primary chick-embryo fibroblast cells and propagating same in primary chick-embryo fibroblast cells after adaptation, which comprises using the rabies virus for adaptation in increasing dilutions of from $10^{-1}$ to $10^{-5}$ and for inoculation of the multiplication cultures in dilution in the range of from $10^{-2}$ to $10^{-5}$.

According to a preferred embodiment the process is carried out at a temperature in the range of from 30° to 38° C, more preferably 32° to 37° C.

For the process of the invention there can be used all rabies strains generally used in the preparation of rabies virus vaccines, for example the Flury, LEP and Flury HEP strains, the rabies virus fixe strain VP 11, the fixe strain Pasteur and the PM strain (PM = Pitman-Moore).

Chick-embryos for the fibroblast cells are cheap, readily acessible and the yield of cells is very good. For use in man there are preferably used chick-embryos of so-called SPF eggs, i.e. eggs of chickens specifically raised free from pathogens in chicken farms run for this purpose. Tissue cultures of SPF eggs are free from undesired foreign viruses as can be observed in eggs of chickens bred in usual manner for example the virus of infectious bursitis, of infectious laryngotracheitis, of influenza type A, of chicken pox, aviary encephalomyelitis, of inclusion hepatitis, of infectious bronchitis, chicken leucosis, of the Marek disease, of the Newcastle disease, of aviary reoviruses, of aviary adeno-viruses, of Mycoplasma gallisepticum, of Mycoplasma synoviae and of Salmonella pullorum. The use of chick-embryo fibroblast cells for the preparation of a rabies vaccine for man is novel and not yet described.

The rabies vaccine is prepared in accordance with the invention by adapting the rabies virus to primary chick-embryo fibroplast cells, propagating the adapted virus in primary chick-embryo fibroplast cells and working up the virus-containing suspension, optionally after inactivation in known manner to obtain a vaccine. The rabies virus adapted according to the invention allows of obtaining in the virus propagation such high virus concentrations that a useful rabies vaccine can be prepared therefrom.

As starting material mammal brain is preferably used, especially the brain of rabbits, containing, for example, viruses of the strain VP 11, the strain Pasteur, or the strain PM, or homogenized chick-embryo material containing for example viruses of the strain Flury LEP or Flury MEP, which is applied to a monolayer cell culture of primary chick-embryo fibroblast cells.

When an undiluted virus material is transferred according to state of the art to infect as high a number of cells as possible, a few cells are populated only and in the following passages the number of infected cells does not increase; it is even reduced. Hence, an adapting of the virus to the cell does not take place and cannot be obtained in this manner.

As compared therewith, when the virus-containing suspension to be used for the passages is diluted to $10^{-1}$ to $10^{-4}$, a rabies virus is obtained which is suitable for the preparation of a rabies vaccine. The decisive fact for the transfer of one dilution to the next higher one is the multiplication kinetics of the virus in the preceding passage. In view of the fact that virus strains can be well propagated at a dilution of $10^{-2}$, there are first made passages with the $10^{-1}$ and $10^{-2}$ dilutions of the starting material.

To control the virus multiplication, infested cover-glass cultures in Leighton tubes, which have been treated in similar manner, are used. When the cover-glass culture is colored with a fluorescin-marked anti-rabies gamma globulin, the dyed preparation can be evaluated under the fluorescence microscope, the percentage of the cell infested with rabies virus indicating the muliplication kinetics. A sufficient number of controls is prepared so that the virus population of the cells can be followed daily. For each reading 1 to 2 tubes are required.

At first, the viruses settle very relunctantly on the cells but during the course of the passages according to the invention the settlement increases.

When, in one passage, 100% of the cells are infested with virus within 3 to 4 days, the $10^{-2}$ or $10^{-3}$ dilution is used and, thereafter, the $10^{-4}$ dilution, if necessary.

With the change to higher dilutions, the virus titer increases during the passages with a settlement of 100% of the cell monolayer.

The virus-containing suspension of the last passage is used as seed material for the virus growth in the preparation of the vaccine. Owing to the high titer of the seed material and the rapid settlement of the cells by the adaptation according to the invention, very little seed material is required in the production so that the valuable material is largely saved. The extensive tests requested by the governments highly increase the costs of the seed material.

To obtain a sufficiently high virus titer in the manufacture of the vaccines 1 $LD_{50}$ of the seed material is required for about 20,000 cells, whereas about 1 to 10 $LD_{50}$ or PFU (plaque forming unit) are necessary according to the state of the art to inoculate one cell.

$LD_{50}$ in the mouse and PFU in tissue are approximately comparable.

The adaptation is reliable and rapid. The virus titers obtained are by ten times or more higher than the titers obtained according to the state of the art. Hence, concentration procedures can be dispensed with. If, however, a concentration step is added, for example for vaccines for man, the virus titer can again be increased to the hundred-fold.

The following examples illustrate the invention.

EXAMPLE 1

Adaptation of a rabies virus and preparation of an inactivated vaccine for use in man and animals.

As starting material the rabies virus fixe strain VP 11 was used, which can be obtained from the World Health Organization, Reference Center for Rabies, Institute Pasteur, Paris, in the form of a lyophilized substance from rabbit brain.

The virus had a titer of $10^{5.2} LD_{50}/ml$, measured by intracerebral injection into white mice of 11 to 15 grams of the family NMRI.

The content of the ampoule was dissolved in 1 ml of aqua destillata and applied on primary chick-embryo fibroblast cells (CEFC) in a dilution of $10^{-2}$.

Seven cover-glass cultures of the same cell preparation in Leighton tubes were also inoculated with the $10^{-2.0}$ dilution (passage I 1). After a time of incubation of 5 days at $+37°$ C, less than 25% of the fibroblast cells had been infected.

The virus-containing cell-free supernatant in the $10^{-1.0}$ dilution was transferred to the 2nd passage of primary chick-embryo fibroblast cells (passage I 2). After a time of incubation of 6 days at $+37°$ C, about 25% of the cells were infested. The cell-free supernatant was transferred in the dilutions $10^{-1.0}$ and $10^{-2.0}$ onto primary CEFC (passage I 3). After a time of incubation of 4 days, with the $10^{-1.0}$ dilution 70% and with the $10^{-2.0}$ dilution 90% of the cells were infested. The passage with the $10^{-1.0}$ dilution was continued with this dilution and the passage carried out with the $10^{-2.0}$ dilution was continued in that dilution.

A new series of passage was branched off, the passage carried through in the $10^{-2.0}$ dilution, which was continued with the $10^{-3.0}$ dilution (passage I 4).

The further course of adaptation is illustrated by the following table:

| passage No. | dilution | harvest/day | % infested cells | virus titer $LD_{50}/ml$ | remarks |
| --- | --- | --- | --- | --- | --- |
| I 5 | $10^{-1}$ | 3 | 75 | | |
| | $10^{-2}$ | 3 | 100 | | |
| | $10^{-3}$ | 3 | 100 | | |
| I 6 | $10^{-1}$ | 3 | 75 | | |
| | $10^{-2}$ | 3 | 100 | | |
| | $10^{-3}$ | 3 | 75 | | |
| I 7 | $10^{-1}$ | 4 | 50 | | |
| | $10^{-2}$ | 4 | 75 | | |
| | $10^{-3}$ | 4 | 100 | | |
| I 11 | $10^{-1}$ | 5 | 25 | | |
| | $10^{-2}$ | 5 | 50 | | |
| | $10^{-3}$ | 5 | 50 | | |
| I 12 | $10^{-1}$ | 3 | 25 | | adaptation of virus strain still insufficient |
| | $10^{-2}$ | 3 | 50 | | |
| | $10^{-3}$ | 3 | 50 | | |
| I 13 | $10^{-2}$ | 3 | 25 | | |
| | $10^{-3}$ | 3 | 75 | | |
| I 17 | $10^{-2}$ | 3 | 80 | $10^{7.1}$ | adaptation of virus strain still insufficient |
| | $10^{-3}$ | 3 | 100 | $10^{7.6}$ | |
| I 18 | $10^{-2}$ | 3 | 75 | $10^{6.9}$ | |
| | $10^{-3}$ | 3 | 95 | $10^{7.2}$ | |
| I 19 | $10^{-2}$ | 3 | 50 | $10^{6.1}$ | |
| | $10^{-3}$ | 3 | 95 | $10^{6.2}$ | |
| I 26 | $10^{-2}$ | 3 | 90 | $10^{7.1}$ | |
| | $10^{-3}$ | 3 | 100 | $10^{8.0}$ | |
| I 27 | $10^{-2}$ | 3 | 100 | $10^{6.3}$ | |
| | $10^{-3}$ | 3 | 100 | $10^{7.4}$ | |
| I 28 | $10^{-2}$ | 3 | 100 | $10^{7.2}$ | |
| | $10^{-3}$ | 3 | 100 | $10^{7.8}$ | |
| I 29 | $10^{-2}$ | 3 | 90 | $10^{6.8}$ | |
| | $10^{-3}$ | 3 | 100 | $10^{7.6}$ | |
| I 30 | $10^{-2}$ | 3 | 90 | $10^{6.9}$ | |
| | $10^{-3}$ | 3 | 100 | $10^{8.0}$ | |
| I 31 | $10^{-2}$ | 3 | 90 | $10^{6.4}$ | strain sufficiently adapted |
| | $10^{-3}$ | 3 | 100 | $10^{7.8}$ | |
| I 31 | $10^{-3}$ | 3 | 100 | $10^{8.0}$ | 1. repetition |
| I 31 | $10^{-3}$ | 3 | 100 | $10^{8.6}$ | 2. repetition |

Passage I 31 constitutes the seed material for an inactivated rabies virus ad.us.hum. It is surprising that in the passages I to 26 to I 31 the virus concentration of the $10^{-3.0}$ dilutions is on the average about 9 times higher than the concentration of the $10^{-2.0}$ dilutions. This fact is confirmed by repeating twice the passage I 31. In the first repetition the virus concentration was 40 times higher and in the second 100 times higher.

Preparation of a vaccine ad us. hum.

Test vaccines were prepared from seed material of the strain Flury LEP adapted to primary chick-embryo fibroblast cells. The seed material, prepared according to the process specified above, was placed in a $10^{-3.0}$ dilution on primary CEFC and incubated at $+32°$ C. After clarification in a continuous flow centrifuge, the harvest of the virus-containing suspension yielded a virus titer of $10^{7.4} LD_{50}/ml$.

The virus was then inactivated in known manner with $\beta$-propiolactone and the vaccine was tested in the NIH test, a mouse-protection test, by comparing it with a standard vaccine having an antigen value of 1.

The virus titer could be further increased. To this end, the virus suspension obtained was further purified in the continuous density gradient and concentrated. In this manner a concentration factor of about 100:1 and a virus titer of $10^{9.3} LD_{50}/ml$ were obtained. The concentrated virus suspension was adjusted to a concentration of 10:1, inactivated with $\beta$-propiolactone and likewise subjected to the NIH test.

The vaccines prepared in accordance with the invention had an antigen value of 1.2 and the vaccines with the 10:1 concentrated virus had an antigen value of 4.8.

It can be seen that the process of the invention makes it possible to prepare a vaccine having a sufficient antigen value for use in man. In the NIH test active vaccines are set free the antigen value of which amounts to at least 30% of the antigen value of a standard vaccine. The vaccine prepared as described above was 1.2 times better than the standard vaccine A 18 tested under identical conditions, which is standardized on the International World Health Organization rabies standard vaccine, and 4.8 times better with the purified and concentrated virus material.

EXAMPLE 2

Adaptation of a production strain and preparation of a rabies virus vaccine for use in animals.

As starting material the rabies virus strain Flury HEP was used, which can be obtained from the American Type Culture Collection in Rockville, Md., USA, in the form of a homogenized and lyophilized substance from virus-containing chick-embryos. The virus was adapted in the manner described in Example 1, with the exception that the cultures were incubated at 32° C and a dilution stage of $10^{-4.0}$ was additionally used. The adaptation of the virus strain HEP took place as follows:

| passage No. | dilution | harvest/day | % infested cells | virus titer $LD_{50}$/ml | remarks |
|---|---|---|---|---|---|
| K 1 | $10^{-2}$ | 4 | 25 | — | |
|  | $10^{-3}$ | 3 | 74 | $10^{5.7}$ | |
| K 2 | $10^{-2}$ | 4 | 25 | — | |
|  | $10^{-3}$ | 4 | 70 | $10^{6.5}$ | |
| K 3 | $10^{-2}$ | 5 | 25 | — | strain not yet |
|  | $10^{-3}$ | 5 | 25 | $10^{4.8}$ | adapted |
| K 7 | $10^{-2}$ | 4 | 100 | — | |
|  | $10^{-3}$ | 4 | 100 | $10^{7.5}$ | |
| K 8 | $10^{-3}$ | 4 | 100 | $10^{6.8}$ | test vaccine |
|  | $10^{-4}$ | 4 | 90 | $10^{7.3}$ | prepared |
| K 9 | $10^{-3}$ | 4 | 100 | $10^{7.3}$ | test vaccine |
|  | $10^{-4}$ | 4 | 90 | $10^{7.5}$ | prepared |
| K 12 | $10^{-3}$ | 3 | 100 | $10^{6.7}$ | |
|  | $10^{-4}$ | 4 | 100 | $10^{7.3}$ | |
| K 13 | $10^{-3}$ | 3 | 100 | $10^{7.0}$ | |
|  | $10^{-4}$ | 3 | 100 | $10^{7.5}$ | |

It can be seen that in this case, too, higher virus titers can be obtained when the next higher dilution of the inoculation material is used for the following passage. Two test vaccines were prepared as follows:

33% of a stabilizer solution consisting of polymerized and decomposed gelatin, which had been prepared as described in German Pat. No. 1,118,792, and sodium glutamate were added to the virus-containing medium of passages K8 and K9. After lyophilization, test vaccine 1 had a virus content of $10^{6.3}$ $TCID_{50}$/ml, while the virus content of vaccine 2 amounted to $10^{7.0}$ $TCID_{50}$/ml.

In the recommendations of the WHO, "Laboratory Techniques in Rabies", 3rd edition, Geneva, virus vaccines should have a minimum titer of $10^{5.2}$ $LD_{50}$ or $TCID_{50}$. In the vaccines prepared according to the invention the virus concentration was more than ten times higher than the required minimum concentration.

EXAMPLE 3

Adaptation of a production strain and preparation of an inactivated vaccine for use in animal.

As starting material the rabies virus strain Flury LEP was used, which can be obtained from the American Type Culture Collection. The strain was used in the form of a lyophilized, virus-containing chick-embryo homogenized product adapted to the cell strain Wi38. The adaptation to primary chick-embryo fibroblast cells was performed according to the invention by using for the series passages dilutions of the infection material slowly progressing in powers of ten in dependence on the percentage of infected cells. The seed material for the preparation of the inactivated commercially available vaccine Madivak was prepared from passage C22 (dilution passage $10^{-3.0}$). It had a virus titer of $10^{7.2}$. According to the invention, the vaccine was prepared with a $10^{-3.0}$ dilution of the seed material or with an intermediate passage treated according to the invention from the seed material prepared as described in Example 1.

The vaccine had an NIH value of 2.6, while a vaccine prepared in accordance with the state of the art, which had been obtained from other tissue cultures (cell strain PK 15) was found to have an antigen value of 0.4 in the NIH test.

What is claimed is:

1. In a process for preparing a rabies vaccine, the improvement wherein the rabies virus is first adapted to chick-embryo fibroblast cell cultures using a suspension containing the rabies virus in progressing dilutions from $10^{-1}$ to $10^{-5}$ for the inoculation of the cell culture passages and then inoculating growth cultures with a suspension containing the adapted rabies virus in a dilution from $10^{-2}$ to $10^{-5}$ for multiplication of the virus.

2. A process as claimed in claim 1, wherein during the passages the temperature is maintained in the range of from 30° to 38° C.

3. A process as claimed in claim 1, wherein during the passages the temperature is maintained in the range of from 32° to 37° C.

4. A process as claimed in claim 1, wherein chick-embryo fibroblast cells of SPF eggs are used for the vaccine production.

* * * * *